United States Patent [19]

Hájek et al.

[11] Patent Number: 4,806,681

[45] Date of Patent: Feb. 21, 1989

[54] PROCESS FOR PRODUCING CINNAMIC ACID FROM 1,1,1,3-TETRACHLORO-3-PHENYLPROPANE

[75] Inventors: Milan Hájek, Prague; Přemysl Šilhav, Říčany, both of Czechoslovakia

[73] Assignee: Ceskoslovenska akademie ved, Czechoslovakia

[21] Appl. No.: 58,610

[22] Filed: Jun. 4, 1987

Related U.S. Application Data

[63] Continuation of Ser. No. 752,975, Jul. 8, 1985, abandoned.

[30] Foreign Application Priority Data

Jul. 12, 1984 [CS] Czechoslovakia ............... 5410-84

[51] Int. Cl.$^4$ .................................. C07C 51/093
[52] U.S. Cl. .................................. 562/422
[58] Field of Search .................. 562/406, 422, 495

[56] References Cited

FOREIGN PATENT DOCUMENTS 0217518 2/1985 Czechoslovakia .

OTHER PUBLICATIONS

Asscher et al., J. Chem. Soc., pp. 1887–1896 (1963).
Goldwhite et al., Tetrahedron, vol. 20, pp. 1649–1656 (1964).

Primary Examiner—Michael L. Shippen
Attorney, Agent, or Firm—Leydig, Voit & Mayer

[57] ABSTRACT

This invention relates to a process for preparing cinnamic acid by hydrolysis of 1,1,1,3-tetrachloro-3-phenylpropane with acetic acid, trifluoroacetic acid or formic acid, optionally in the presence sulphuric acid, phosphoric acid, para-toluenesulphonic acid, or a cation exchange resin containing sulphonic acid groups. The mixture is heated at a temperature from about 80° to about 150° C. until hydrogen chloride evolution ceases, after which time the cinnamic acid is separated.

2 Claims, No Drawings

PROCESS FOR PRODUCING CINNAMIC ACID FROM 1,1,1,3-TETRACHLORO-3-PHENYLPROPANE

This application is a continuation, of application Ser. No. 752,975, filed July 8, 1985, now abandoned.

The invention relates to a process for producing cinnamic acid from 1,1,1,3-tetrachloro-3-phenylpropane.

Cinnamic acid has been recently used as an inhibitor of corrosion of zinc plates, in removing of boiler incrustation and spray packings, as a thermal stabilizer of poly(vinyl chloride), a crosslinking catalyst for dimethylterephthalate-ethylene glycol polymers and polyurethanes and as a flame retardant for caprolactame. Furthermore, cinnamic acid is a valuable intermediate for drug synthesis and its esters are used in cosmetic industry as a component of fragrant compositions. Lately, the acid has increasingly been used as a starting material in the enzymatic transformation to L-phenylalanine which together with L-aspartic acid is a component of a novel artificial sweetener.

The common process for producing cinnamic acid is Perkin synthesis, i.e. the condensation of benzaldehyde with acetanhydride in the presence of alkali metal acetates. The reaction requires high temperatures around 180° to 185° C., and at reaction times from 8 to 17 h the acid is obtained in 80 to 85% yields.

The processes disclosed in latest Japan patents are based on the reaction of styrene, an alcohol and carbon monoxide in the presence of platinum or palladium catalysts to give cinnamic acid esters, however with the lower selectivity (Jap. Pat. No. 57 070 836 (1980), Jap. Pat No. 56 071 039 (1979); Chem. Abstr. 95, 186892 (1981)).

The process for producing cinnamic acid of this invention starts from 1,1,1,3-tetrachloro-3-phenylpropane which is easily available by the radical addition of tetrachloromethane to styrene, as disclosed in Czech Pat. No. 209 347. The hydrolysis of this adduct in an acidic medium produces cinnamic acid.

It is known from the art that the hydrolytic reactions of the adduct afford the acid with low selectivity and at slow reaction rates. Thus, for example, the hydrolysis of 1,1,1,3-tetrachloro-3-phenylpropane with concentrated perchloric acid gave cinnamic acid in only 35% yield (J. Chem. Soc. 1887 (1963)). It has been further reported that high yields of the acid (around 90 per cent) are achieved by hydrolysis with the use of ferric chloride in acetic acid (Tetrahedron 20, 1649 (1964)). The disadvantage of this process is a large amount of ferric chloride that impedes purification of the crude cinnamic acid and of waste waters.

This invention relates to Czech. Pat. No. 217 518 in that it utilizes the finding that hydrolysis of 1,1,1,3-tetrachloro-3-phenylpropane can be effected catalytically in the presence of Lewis acids such as zinc and tin compounds in acetic acid. This process is highly selective, proceeds at high reaction rates, giving cinnamic acid in high yields. Industrial application of this process is not, however, without difficulties: it requires a complicated equipment for absorption of violently evolving hydrogen chloride, the difficult manipulation with solidifying reaction mixture and the difficult purification of waste waters. The acid so obtained is of lower purity and requires costly purification.

According to the invention there is provided a process for producing cinnamic acid by hydrolysis of 1,1,1,3-tetrachloro-3-phenylpropane, which comprises heating a mixture containing 1 part by weight of 1,1,1,3-tetrachloro-3-phenylpropane with 0.1 to 5 parts by weight of 80 to 100% acid such as acetic acid, trifluoroacetic acid or formic acid, eventually in the presence of up to 1 part by weight of 50 to 100% additional acid such as sulphuric, phosphoric, or p-toluenesulphonic acid or in the presence of up to 10 parts by weight of a cation exchanger containing sulphonic acid groups to temperatures in the range 80° to 150° C., eventually with gradual addition of up to 10 parts by weight of water until hydrogen chloride evolution ceases.

When 1,1,1,3-tetrachloro-3-phenylpropane is converted into cinnamic acid with the use of trifluoroacetic or formic acid, the addition of another strong acid is not necessary. The reaction in formic acid is accompanied by a partial decomposition of the acid to carbon monoxide and water. The remaining formic acid can be, however, recovered by distillation and reused in the process. In the case of acetic acid, it is advantageous to add (a) water, (b) water-containing inorganic acid or (c) p-toluenesulphonic acid and acetic acid to ensure a fluent evolution of hydrogen chloride.

The process for producing cinnamic acid from 1,1,1,3-tetrachloropropane according to this invention is easy to perform, is economically advantageous and gives the product in high yield and purity. The process proceeds at the higher reaction rate and with the higher selectivity at a fluent evolution of hydrogen chloride.

Embodiments of the invention are particularly described with reference to the following non-limitative Examples.

As used in the following examples Wolfatit OK 80 is a sulfonated polystyrenedivinylbenzene resin having high porosity and a high surface area of $35 m^2/g$ and Ostion KSC is a sulfonated polystyrene-divinylbenzene resin having low porosity and a low surface area of $1.1 m^2/g$.

EXAMPLE 1

A mixture of 129 g of 1,1,1,3-tetrachloro-3-phenylpropane, 74 g of glacial acetic acid and 4.9 g of 98% sulphuric acid is stirred and heated to the boiling point 117° to 122° C. while adding water for 15 h, after which time hydrogen chloride evolution ceases. By cooling the reaction mixture, 54.8 g of cinnamic acid is precipitated. The acid is separated by filtration, washed with water, the filtrate is condensed by solvent evaporation, which yields another 7.4 g of cinnamic acid. The total yield is 84 per cent. The melting point of recrystallized cinnamic acid from diluted acetic acid is 133° to 134° C. and its purity exceeds 99 per cent.

EXAMPLE 3

A mixture of 129 g of 1,1,1,3-tetrachloro-3-phenylpropane, 74 g of glacial acetic acid, and 31 g of monohydrate of p-toluenesulphonic acid is heated while stirring to the boiling point 115° to 120° C. for 13 h with gradual addition of 18 g of water. The precipitated crystals are filtered off, washed with water, to give 59 g of cinnamic acid. Then, the filtrate, is condensed, crystals are filtered off and washed with water to give another 11 g of cinnamic acid with the total yield of 94.5% (melting point 131° to 133° C., min. 98% purity).

EXAMPLE 4

A mixture of 129 g of 1,1,1,3-tetrachloro-3-phenylpropane, 74 g of glacial acetic acid and 39 g of Wolfatit OK 80 cation exchanger is heated to 118° to 124° C. for 15 h. The cation exchanger is removed from the hot reaction mixture by filtration. After cooling the mixture, filtration of the crystals and their washing with water, 56.5 g of cinnamic acid is obtained. Condensation of the filtrate followed by filtration of the crystals gives another 9.5 g of cinnamic acid with total yield of 89% (melting point after recrystallization 128° to 135° C., min. 98% purity).

EXAMPLE 5

A mixture of 25.8 g of 1,1,1,3-tetrachloro-3-phenylpropane, and 22 g of 80% trifluoroacetic acid is heated under stirring to 80° to 90° C. for 2 h. After dilution of the reaction mixture with water to 1:1 ratio and cooling, filtration of the crystals gives after their washing with water 15.2 g of cinnamic acid in 96% yield (melting point 127° to 133.5° C., min. 97% purity).

EXAMPLE 6

A mixture of 129 g of 1,1,1,3-tetrachloro-3-phenylpropane and 100 g of 85% formic acid is heated to 100° to 106° C. for 10 h. Te reaction is accompanied by evolution of hydrogen chloride and carbon monoxide. Cooling the reaction mixture, filtration of the crystals and their washing with water affords 60 g of cinnamic acid in 81% yield (melting point 126° to 132° C., purity over 97per cent).

EXAMPLE 7

A mixture of 103.2 g of 1,1,1,3-tetrachloro-3-phenylpropane, 114 g of 85% formic acid and 4.2 g of 93% sulphuric acid is refluxed under stirring at a temperature in the range 100° to 110° C. for 6 h with evolution of hydrogen chloride and carbon monoxide. The reaction mixture is cooled, the crystals so precipitated are filtered off and washed with water to give 51.5 g of cinnamic acid in total yield of 98 per cent (melting point 127° to 133° C., min. 98% purity).

EXAMPLE 8

A mixture of 103.2 g of 1,1,1,3-tetrachloro-3-phenylpropane, 120 g of 85% formic acid and 17 g of Ostion KSC cation exchanger is refluxed at 100° to 105° C. for 7 h while hydrogen chloride and carbon monoxide is evolved. The cation exchanger is separated by filtration, the filtrate is cooled and the crystals precipitated are filtered off and washed with water to give 46.8 g of cinnamic acid in 79% chemical yield (melting point 127° to 133.5° C. and min. 97% purity).

EXAMPLE 9

A mixture of 51.6 g of 1,1,1,3-tetrachloro-3-phenylpropane, 60 g of glacial acetic acid and 17.8 g of 55% sulphuric acid is refluxed under stirring at 115° to 122° C. for 5 h, after which time the evolution of hydrogen chloride ceases. The work-up of the reaction mixture as described in Example 1 yields 22.5 g and 2.9 g of cinnamic acid in 85.8% total yield (melting point 131.5° to 133° C., min. 99% purity).

EXAMPLE 10

A mixture of 77.4 g of 1,1,1,3-tetrachloro-3-phenylpropane, 7.7 g of 98% acetic acid and 1.8 g of 98% sulphuric acid is stirred and refluxed at 130° to 138° C. while a mixture of 15.5 g of water, 4 ml of acetic acid and 0.5 ml of sulphuric acid is gradually added over the period of 2.5 h, after which time the hydrogen chloride evolution ceases. The work-up of the reaction mixture as described in Example 1 gives 33.6 g of cinnamic acid in 75.6% total yield (melting point 132° to 133° C., min. 99% purity).

We claim:

1. A process for preparing cinnamic acid by hydrolyzing 1,1,1,3-tetrachloro-3-phenylpropane consisting essentially of heating the 1,1,1,3-tetrachloro-3-phenylpropane in the presence of an acidic composition consisting essentially of from 0.1 to 5 parts by weight of acetic acid having a concentration of 80% to 100% and a strong acid having a concentration of 50 to 100%, which is present in an amount up to one part by weight, said strong acid being selected from the group consisting of sulfuric, phosphoric, and para-toluenesulphonic acid, said heating being at a temperature in the range from 80° to 150° C., causing evolution of hydrogen chloride, gradually adding water to the reaction mixture, in an amount up to 10 parts by weight, during the period of hydrogen chloride evolution, and subsequently separating the cinnamic acid.

2. A process for preparing cinnamic acid by hydrolyzing 1,1,1,3-tetrachloro-3-phenylpropane consisting essentially of heating the 1,1,1,3-tetrachloro-3-phenylpropane in the presence of an acidic composition consisting essentially of from 0.1 to 5 parts by weight of acetic acid having a concentration of 80% to 100% and a cation exchange resin containing sulphonic acid groups, which is present in an amount up to ten parts by weight, said heating being at a temperature in the range from 80° to 150° C., causing evolution of hydrogen chloride, gradually adding water to the reaction mixture, in an amount up to 10 parts by weight, during the period of hydrogen chloride evolution, and subsequently separating the cinnamic acid.

* * * * *